United States Patent [19]
Cassaday

[11] Patent Number: 6,150,182
[45] Date of Patent: Nov. 21, 2000

[54] METHOD FOR SEPARATION OF COMPONENTS IN A BIOCHEMICAL REACTION UTILIZING A COMBINATION OF MAGNETIC AND CENTRIFUGAL PROCESSES

[76] Inventor: Michael M. Cassaday, Four Todd La., Somers, N.Y. 10589

[21] Appl. No.: 09/201,010

[22] Filed: Nov. 30, 1998

[51] Int. Cl.⁷ .................... G01N 33/553; G01N 35/00; G01N 35/08; G01N 15/06; C12Q 1/66

[52] U.S. Cl. .................... 436/526; 436/45; 436/52; 436/518; 436/523; 436/534; 436/524; 436/806; 436/807; 436/824; 435/971; 435/8; 422/681; 422/69; 422/72; 210/222; 210/223; 210/695

[58] Field of Search .................... 436/45, 52, 518, 436/523, 524, 526, 534, 806, 807, 824; 422/68.1, 69, 72; 435/971, 8; 210/222, 223, 695

[56] References Cited

U.S. PATENT DOCUMENTS

| | | | |
|---|---|---|---|
| 4,017,385 | 4/1977 | Morton et al. | 209/214 |
| 4,935,147 | 6/1990 | Ullman et al. | 210/695 |
| 5,098,845 | 3/1992 | Babson | 436/45 |
| 5,147,529 | 9/1992 | Lee et al. | 210/695 |
| 5,224,604 | 7/1993 | Duczmal et al. | 209/12 |
| 5,258,309 | 11/1993 | Babson | 436/45 |
| 5,422,018 | 6/1995 | Saunders et al. | 210/787 |
| 5,466,574 | 11/1995 | Liberti et al. | 435/5 |
| 5,536,475 | 7/1996 | Moubayed et al. | 422/101 |
| 5,536,644 | 7/1996 | Ullman et al. | 435/7.25 |
| 5,541,072 | 7/1996 | Wang et al. | 435/7.21 |
| 5,560,830 | 10/1996 | Coleman et al. | 210/695 |
| 5,691,208 | 11/1997 | Miltenyi et al. | 436/526 |
| 5,795,470 | 6/1995 | Wang et al. | 210/222 |
| 5,855,848 | 3/1994 | Zuccato | 422/72 |
| 5,866,000 | 11/1997 | Yeh | 210/695 |
| 5,866,071 | 3/1996 | Leu | 422/72 |
| 5,876,593 | 9/1990 | Liberti et al. | 210/95 |
| 5,922,211 | 3/1996 | Nees | 210/781 |

Primary Examiner—Christopher L. Chin
Assistant Examiner—Pensee T. Do
Attorney, Agent, or Firm—Ference & Associates

[57] ABSTRACT

A method for combining magnetic and centrifugal extraction techniques in a manner that improves wash efficiency and reduces the relative disadvantages of stand alone magnetic or centrifugal systems is provided. Centrifugation occurs about the rotational axis of a generally circular container with generally vertical sides featuring an inward protruding physical feature designed to retain material that exceeds the density of supernatent liquid and that is bound to magnetic particles during the centrifugation. During centrifugation, an external magnetic field is applied about the rotational axis of the container such that magnetic lines of force penetrate the container in any desired location. The magnetic and centrifugal forces may be independently modulated or modulated in relative unison to suit the hydrodynamic characteristics of a given complex.

15 Claims, 7 Drawing Sheets

METHOD FOR SEPARATION OF COMPONENTS IN A BIOCHEMICAL REACTION UTILIZING A COMBINATION OF MAGNETIC AND CENTRIFUGAL PROCESSES

Chemical and immune reactions often require the complete removal of un-reacted or unbound chemical components prior to obtaining or detecting an analyte of interest. Effective separation methodologies require maximizing the removal of unbound material while preserving the integrity of the bound material during a wash process. Multiple washes require a rapid execution of wash and rapid cycling between washes to maximize process throughput. This invention relates to a new and unique combination of centrifugal and magnetic forces to effect a rapid and nearly complete separation of unwanted components, preserve a consistent aliquot of bound material, and offer maximum cycling speed.

BACKGROUND OF THE INVENTION

Certain chemical and biological reactions are comprised of one or more intermediate steps where a reaction component is introduced for coupling with a suspected analyte contained in a sample such as blood or urine. Un-reacted portions of this intermediate reagent must be removed prior to additional steps in the reaction or prior to final detection or extraction of the analyte of interest.

For example, a fluorescence generating reagent may be added to reaction products to enable photometric detection of a specific analyte. This detection reagent is designed to bind to the analyte of interest. Detection reagent that has coupled with the complex of interest will yield a photometric signal in direct proportion to the quantity of complex present only if unbound fluorescence generating reagent is removed or otherwise deactivated. Free flouresence generating reagent that is not removed constitutes interference or background noise in the signal detection process and may lead to false positives or inaccurate quantitative analytical results.

Current immunoassay analysis contains many such reactions where one or more chemical components must be removed while preserving the integrity and quantitative accuracy of the original species of interest. Several techniques have evolved to assure complete removal of unwanted components in a cycle generally termed a wash cycle.

One such technique is to coat the inner surfaces of a container or well, such as a microtiter plate, with an antibody or antibody complex selected to bind to an analyte of interest. Blood or other sample is placed in the well. The analyte, if present in the sample, will combine with the complex predisposed on the container surface. A wash step follows to remove unreacted sample. A typical wash process consists of removal of liquid by an aspirating probe followed by the addition and removal of a rinse solution. Additional chemical components such as a radioactive label or a fluorescent tag may be introduced, reacted and removed by repeating this basic wash cycle. The original analyte remains bound to the container wall and available for reaction with subsequent reagent throughout all washing steps.

Immunoassay and other similar binding assays can be very sensitive, detecting extremely minute quantities of an analyte. An interfering material remaining from an incomplete wash may render the test inaccurate. Wash efficiency is thus an extremely important part of such analytical techniques.

Wash efficiency is governed by the quantity of unwanted, unbound material remaining after removal of the supernatant, the volume of rinse added, the quantity of desired, bound material that is inadvertently removed and the total number of wash cycles required. The quantity of unbound material remaining after n number of wash cycles may be expressed by $(Z/Q)^n$, where Z is the volume remaining after decanting and Q is the volume of rinse solution added. To achieve residuals in the nanogram range Z must be very small, Q maximized or the number of wash cycles, n, must be increased.

Increasing n, the number of cycles, has the disadvantage of slowing analytical throughput and increasing the probability of loss of desired, bound material. Wash cycles are time consuming and detract from processing speed in automated analytical instruments. Washing consumes significant quantities of rinse fluid which may contain expensive chemicals. Excessive or over vigorous washing may detach and remove or damage the analyte of interest. Expensive mechanisms and precisely molded containers are required to accurately place aspirating probes to achieve the lowest possible residue after decanting.

The above described coated container is reasonably efficient at washing contained volumes on the order of 100 microliters. Two significant limitations exist with coated containers. The first limitation is one of sensitivity due to the limited surface area available for coating. Attempts to increase surface area by roughening or providing other protruding features generally come at the expense of increasing the residual volume, Z, remaining after a wash decanting. The second limitation involves the volume of the container which serves to limit the rinse volume applicable at each wash cycle.

Another popular separation technique utilizes coated magnetic particles. Here small magnetic particles are coated with a material that is capable of binding an intermediate coupling agent such as antibodies. A reagent solution is comprised of coated particles coupled to specific antibodies disposed in a liquid carrier. A magnet is used to retain bound particles from loss during the rinse portion of a wash cycle. Magnetic particles offer improved sensitivity and speed of reaction due to the large available surface area when compared to coated containers. Particles pose no specific limitation on the volume of rinse cycle. Certain problems, however, exist with magnetic particles during a wash process. These problems include the extended time required to draw magnetic particles out of suspension by application of magnetic force, the magnetic particle collected mass or clumps tend to retain excessive fluid, and the clumped mass is difficult to re-suspend into solution.

A finite time is required to draw particles from suspension into a clumped mass necessary before decanting of rinse fluid can begin. The clumped mass generally remains wet with trapped unbound material effectively increasing the volume Z of unwanted material left behind on each wash cycle. One solution is to agitate and break up the clump in the presence of rinse fluid to improve the removal of unbound material on the next extraction—decant cycle. The problem with re-suspension is the time involved to both suspend and again magnetically attract the suspended particles. There is also increased risk of de-coupling and loosing analyte during such re-suspension efforts.

Magnetic particles differ in magnetohydrodynamic characteristics from lot to lot and within the same sample, thus, some percentage of particles do not magnetically extract in the time allotted for extraction and are lost in the rinse decant. The binding strength of the coating to the particle and the coating to the analyte is finite, restricting the intensity of fluid addition and re-suspension agitation to below levels that tend to exceed said binding strength.

The combination of extra washes required to remove unbound material with losses of some bound material on each wash cycle leads to quantitative errors using this type of assay. The hydrodynamic characteristics of particles, the hydrodynamic characteristics of particles bound to analyte and the precision of the wash cycle must all be carefully controlled to achieve a trustworthy wash process.

Magnetic particle technology continues to advance in performance of the particles and in the wide variety of substances available for binding, capture and extraction.

Yet another method of separation is described by Babson et. al. in U.S. Pat. No. 5,098,845. This patent describes a circular vessel containing a small sphere to which antibodies are attached. Wash separation is effected by rotating the cup about its longitudinal axis where centrifugal force serves to remove the liquid contents while the sphere remains in place. This approach is quite effective in rapidly removing all but the smallest traces of unbound material. Rinse water can be added while the container is spinning to remove the last traces of unbound material without stopping for re-suspension as in the case of magnetic particle separation. The method of Babson et al. has disadvantages similar to coated containers in that the surface area available for binding is limited to the dimension of the sphere.

SUMMARY OF THE INVENTION

The present invention includes a method for combining magnetic and centrifugal extraction techniques in a manner that improves wash efficiency and reduces the relative disadvantages of stand alone magnetic or centrifugal systems. The present invention uses a generally circular container with generally vertical sides featuring an inward protruding circular lip, depression or other physical feature designed to retain material that exceeds the density of supernatent liquid and that is bound to magnetic particles during centrifugation about the longitudinal axis of the container. An external magnetic field is applied to the container such that magnetic lines of force penetrate the container in any desired location. Relative motion between the container and magnetic field may be achieved by moving the container relative to the magnetic field or the magnetic field relative to the container or any desirous combination of relative motion between magnetic forces, centrifugal force and gravitational forces to achieve maximum wash efficiency, or the motion of the container and magnetic field may be synchronized. When magnetic and centrifugal forces are combined, each can be independently modulated or modulated in relative unison to suit the hydrodynamic characteristics of a given complex.

DETAILED DESCRIPTION OF THE INVENTION

Figure 1:
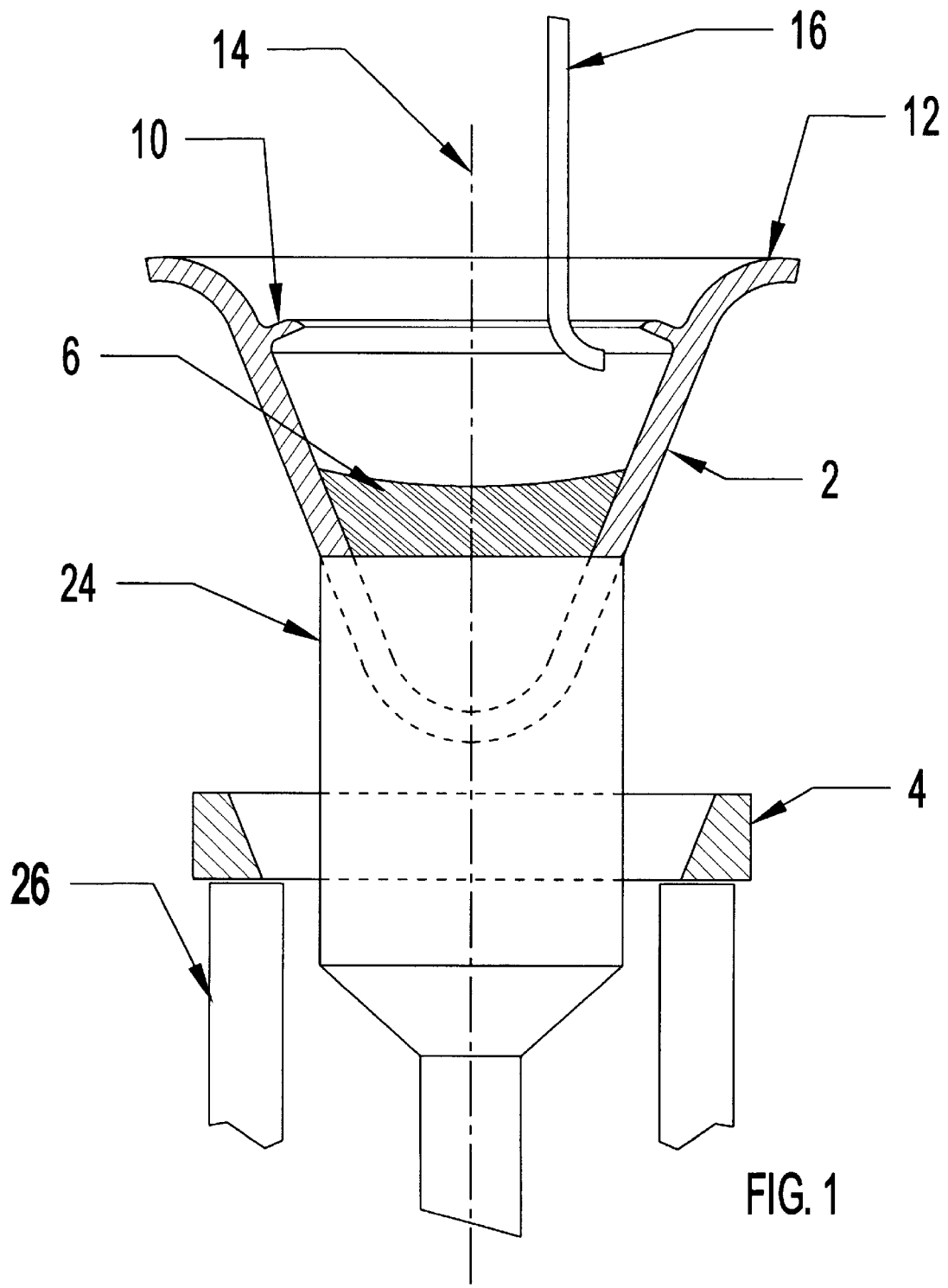
FIG. 1 shows magnetic material suspended in solution with a magnet removed from influence over the suspended material in accordance with an embodiment of the present invention.

The present invention combines magnetic and centrifugal extraction techniques in a manner that improves wash efficiency and reduces the relative disadvantages of stand alone magnetic or centrifugal systems. A generally circular container with generally vertical sides is used in the invention. The container features an inward protruding circular lip, depression or other physical feature designed to retain material that exceeds the density of supernatant liquid and that is bound to magnetic particles during centrifugation about the rotational axis of said container. The shape and dimensions of said lip, depression or structure are configured to trap a given quantity of bound solid phase under the influence of either magnetic or centrifugal forces or a combination of both magnetic and centrifugal forces.

An external magnetic field is applied to the container such that magnetic lines of force penetrate the container in any desired location. The magnetic field may be generated by a series of movable magnets, a ring magnet capable of moving about the external surface of the container, a ring magnet capable of both moving along the longitudinal axis and rotating with said container, an electromagnetic with several individual coils capable of steering the location of the magnetic field or any other directable, positionable magnetic source familiar to those skilled in the art, capable of attracting and positioning magnetic particles within the container, either while the container is rotating or stationary. Relative motion between the container and magnetic field is important and it is obvious that said relative motion can be achieved by moving the container relative to the magnetic field or the magnetic field relative to the container or any desirous combination of relative motion between magnetic forces, centrifugal force and gravitational forces to achieve maximum wash efficiency as described above.

An assay wash step or a biological extraction is performed as described below. The separation sequence described herein represents only one of several possibilities. The exact sequence chosen depends on assay parameters such as relative density of particle complex to background liquid, viscous drag of the complex, migration velocity of complex in a given magnetic field and volume of assay. The benefit of combining magnetic and centrifugal forces is that each can be independently modulated or modulated in relative unison to suit the hydrodynamic characteristics of a given complex.

A biological sample, optional conditioning or diluting reagents, and magnetic particles coated with a substance to bind a component of interest are dispensed into the container. The container may be agitated either about its longitudinal axis or by other suitable means to assure mixing and maximum binding efficiency.

Extraction of desired bound material is accomplished by separation of the bound magnetic particles from the background liquid with the following, one of many, possible sequences:

A magnet approaches the container from the bottom and begins to pull complex toward the walls and bottom of the container;

The container begins to spin slowly forcing liquid against the walls, thereby assisting magnetic extraction by reducing the distance particles must travel to reach sedimentation along said walls. The magnet continues to travel towards the top of the container pulling more complex to the walls and off the bottom of the container;

Rotational velocity increases filling the center of the liquid with an air vortex. Additional complex is driven to the walls and upward by the combined influence of centrifugal and magnetic forces;

The magnet comes to rest near the above described circumfrential lip as rotational speed increases. All magnetic complex has now left the central portions of the container with the majority of particles resting in the space below the lip and against the container inner wall;

The container spins up to very high speed. All liquid volume greater than the volume trapped under the lip overflows the lip and exits the rim of the container. Prolonged centrifugation serves to pack the mass of magnetic particles driving any free liquid out of the container or into a pool atop the packed particles. A jet of rinse liquid may be directed just under the lip at this time to provide additional rinsing;

The container slows to a stop. Any remaining liquid falls to the bottom of the container while bound magnetic material is held under the lip by magnetic force;

An aspirating probe enters the container and removes the majority of remaining liquid at the container bottom;

The magnet is removed. The container is slowly spun while rinse fluid is directed by a dispense probe situated to direct liquid under the lip at the compact mass of particles, thereby loosening and re-suspending bound particles into fresh liquid;

Short bursts of rotation serve to raise the liquid level to the lip, but not over the lip assuring complete and uniform resuspension.

The entire process of compaction, extraction of residual liquid and complete resuspension are possible in a time period on the order of several seconds allowing for rapid processing. Furthermore, the nearly complete removal of all unbound material on each cycle allows fewer cycles to achieve a given final background level of unwanted, unbound material.

Several individual, centrifugal, magnetic stations can be incorporated in an automated machine to increase throughput.

It will become readily apparent that the sequence of events, intensity of magnetic and centrifugal fields and timing of each operation can be adjusted in real time during the separation process to achieve maximum yield and speed for materials of varying characteristics and volumes. It is also possible to program each of several wash stations to execute a different and optimum cycle suitable for the reaction components placed therein.

The quantitative accuracy of most assays is related to the quantity of magnetic particles present for capture of the analyte of interest. A secondary benefit of the invention relates to the quantitative accuracy of said container device and process. Material captured by the container lip is consistent in volume for a given individual container geometry. The container can be easily molded to be precise among containers. The quantity of particles available for assay is, therefore, not dependent on the quantity of particles originally added to the well but is dependent on the quantity of particles remaining under the lip after the first separation cycle, provided the original added quantity is in excess of the lip entrained volume. This allows one to dispense magnetic particle reagent with a pump of reduced accuracy thereby saving the cost of an accurate metering device. It also reduces demands on homogeneity of particle suspension in the particle supply reservoir as the percentage of particles to liquid is governed by volume trapped under the lip and the volume of liquid added after the first wash cycle and not necessarily by volume or ratio of particles to liquid originally added. This constant volume combined with a low loss of particle during the wash assures excellent assay repeatability.

Another advantage of the invention relates to electrical currents generated in any conductive liquid or conductive particles moving in a magnetic field. These currents may damage certain assays, may generate heat in the solution and counter electromotive forces may adversely interact with particle packing schemes, however, those skilled in the art readily appreciate that counter electromotive forces can be used to enhance packing forces by appropriate juxtaposition of the container lip, magnetic and centrifugal forces. Additionally the magnetic field need not be applied during rapid rotation for many successful extraction scenarios. It is also possible to spin the magnet at the same rotational velocity as the cup or rotate an electrically generated magnetic field in synchronization with the spinning cup, thereby, avoiding high speed relative motions between conductors and field.

An advantage of induced electric currents can be made with electro luminescence assays as described in U.S. Pat. No. 5,632,956. This patent describes a method of detecting the presence of an analyte bound to a material that emits light when exposed to an electric current. The present invention not only provides the apparatus and means for washing unbound material in heterogeneous versions of these assays but also provides a means to generate electrical currents within the sample by means of differential movement of magnet and conducting liquid.

It will be further appreciated by those skilled in the art of hydrodynamics that the combination of magnetic and centrifugal forces serves to better capture and rinse very large molecular structures such as protein or cellular material that exhibit high viscous drag and tends to pack in overly wet and large clumps. Viscous drag slows magnetic only compaction, increases particle loss during rinse cycles and the large, wet clumps tend to hold excessive residual unbound material. The present invention rapidly extracts such material and compacts loose clumps to remove a far greater quantity of unbound liquid with lower potential for particle loss on each wash cycle.

Referring now to FIG. 1, a sample container for use in separation is shown in cross-section, generally at 2, which features a retaining lip 10 and an overflow rim 12. A ring magnet 4, is situated below the container in a position sufficiently far from magnetic particle suspension 6 so as not to be of influence on or extract said particles from suspension. A wash probe 16 is illustrated in a position below lip 10 with discharge directed just below rim of said lip. The container 2 is disposed on rotating drive device 24, capable of rotating cup at various speeds about rotation axis 14. Magnetic positioning device 26, is disposed to supporting, rotating and translating magnet 4 along cup axis 14.

Referring to FIGS. 2a through 2d, similar figures indicating the sequences of events in an extraction process. Rotational support device 24 and magnet positioning device 26 are not shown for clarity but it is understood that said support and positioning devices are present and active to rotate cup and raise magnet as indicated in the following described sequence.

Figure 2A:
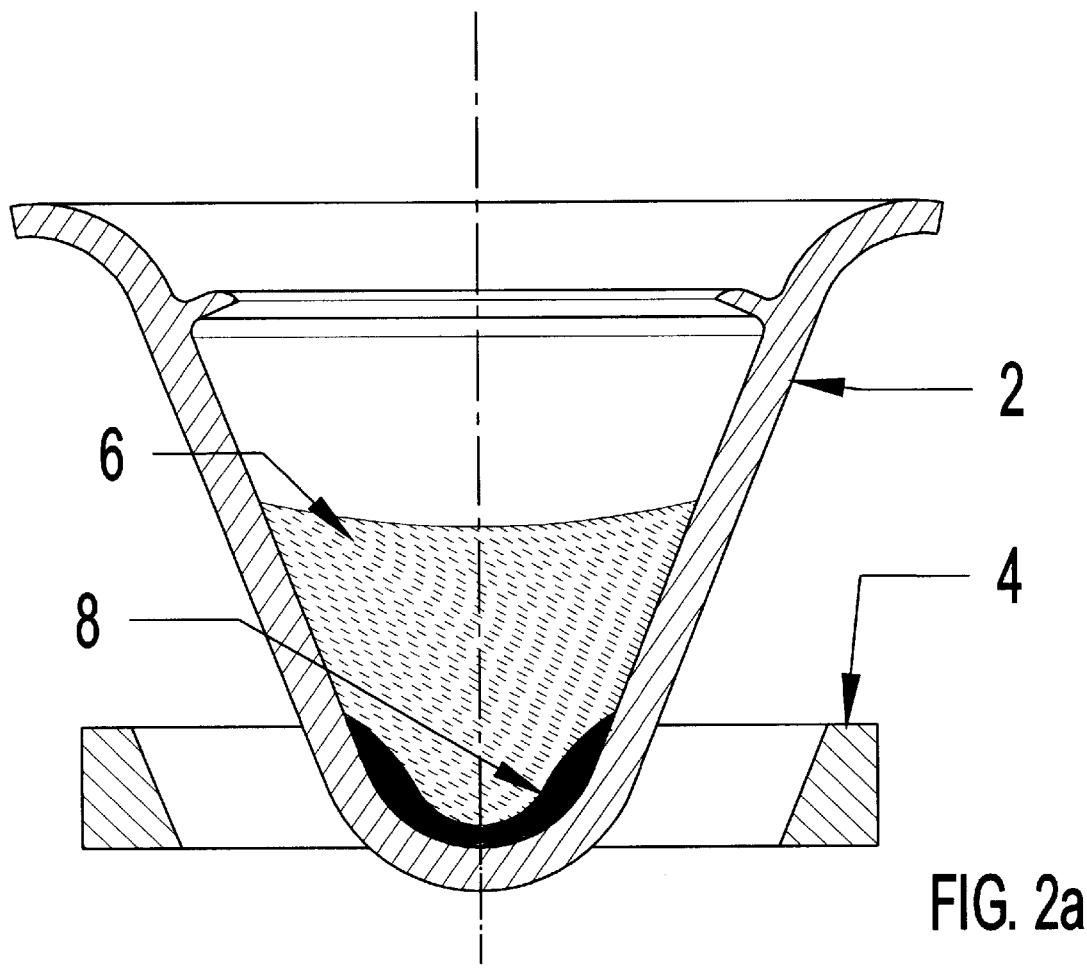
FIG. 2a shows magnetic material being removed from solution during movement of a magnet in accordance with an embodiment of the present invention.

FIG. 2a shows magnet 4 approaching container 2 from the bottom. The magnetic field of magnet 4 begins to exert influence on magnetic particles contained within container 2 thereby extracting a portion of said particles into a compact mass or clump as indicated at 8.

Figure 2B:
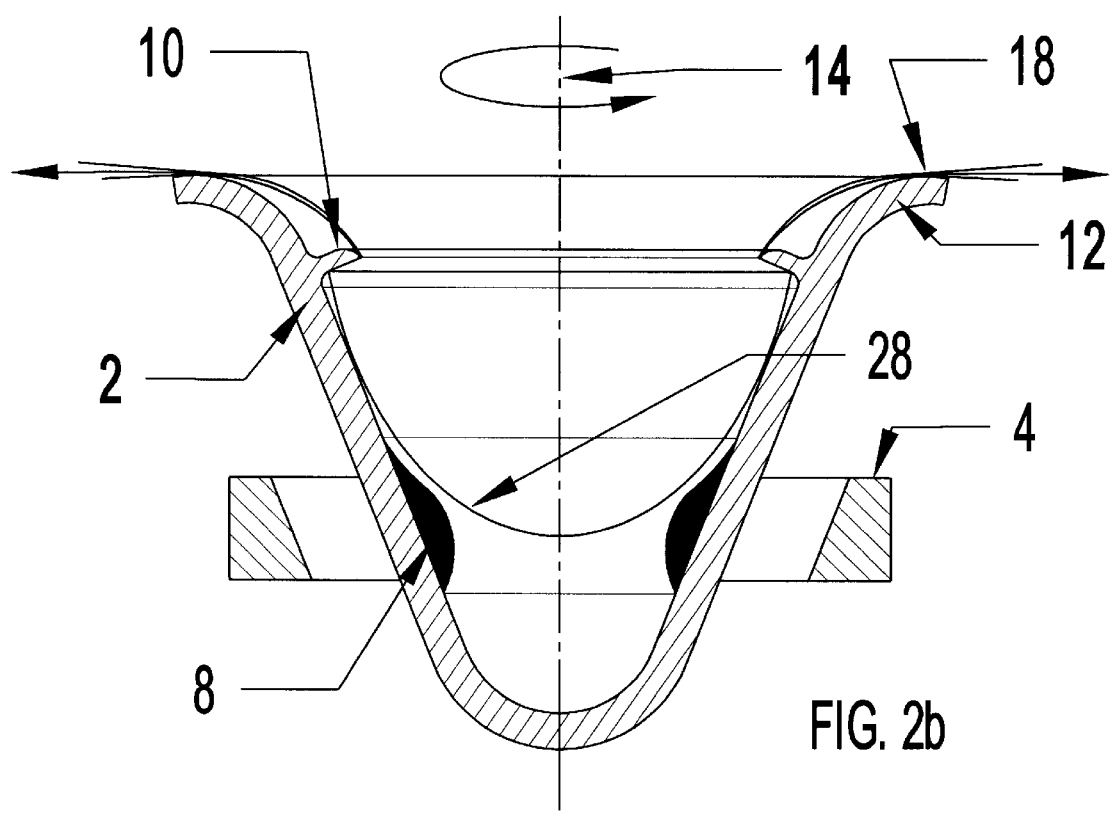
FIG. 2b shows magnetic material being localized as a magnet continues to move and the container begins to spin in accordance with an embodiment of the present invention.

FIG. 2b shows the magnet 4, continuing upwards and exerting a continuing and accumulative influence on magnetic particles, extracting same into a larger clump 8. The container 2 begins to slowly spin about axis 14 drawing the liquid meniscus 28, into a generally parabolic vortex shape terminating below rim 10. The combined influence of magnetic and centrifugal forces tend to pull an ever increasing quantity of particles into clump 8 and force said clump to flow along with and follow the combined resultant of magnetic and centrifugal forces. The majority of particles have been stripped from the liquid supernatant as magnet 4 approaches container rim 10 whereupon container rotational velocity is increased to extract the last remaining particles. Increased rotational velocity begins to force liquid over lip 10 and out over rim 12 as indicated in 18. The fluid passing over the rim is free of any magnetic particles.

Figure 2C:
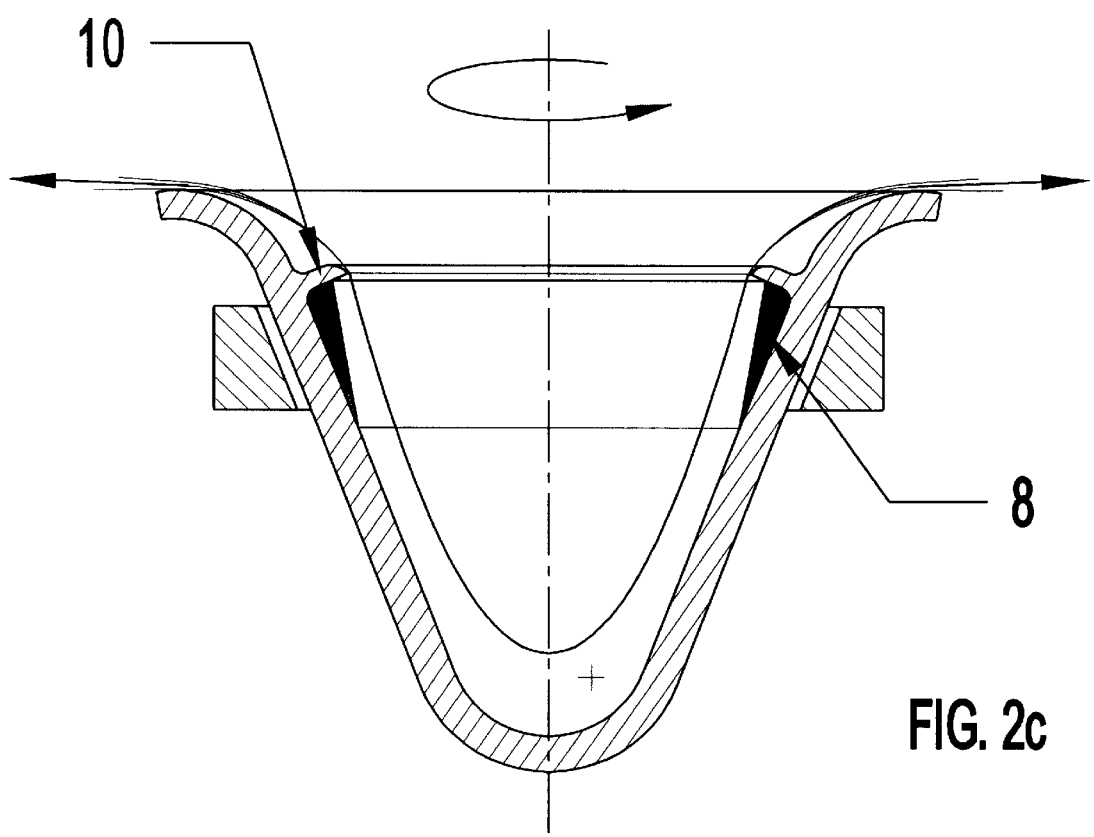
FIG. 2c shows magnetic material being held under a retaining lip by a magnet while the container continues to spin at increased speed expelling supernatant in accordance with an embodiment of the present invention.

FIG. 2c illustrates the process of consolidating the particles 8 into an ever more compact clump 8 near lip 10 and the removal of additional particle free supernatant as rotational speed increases.

Figure 2D:
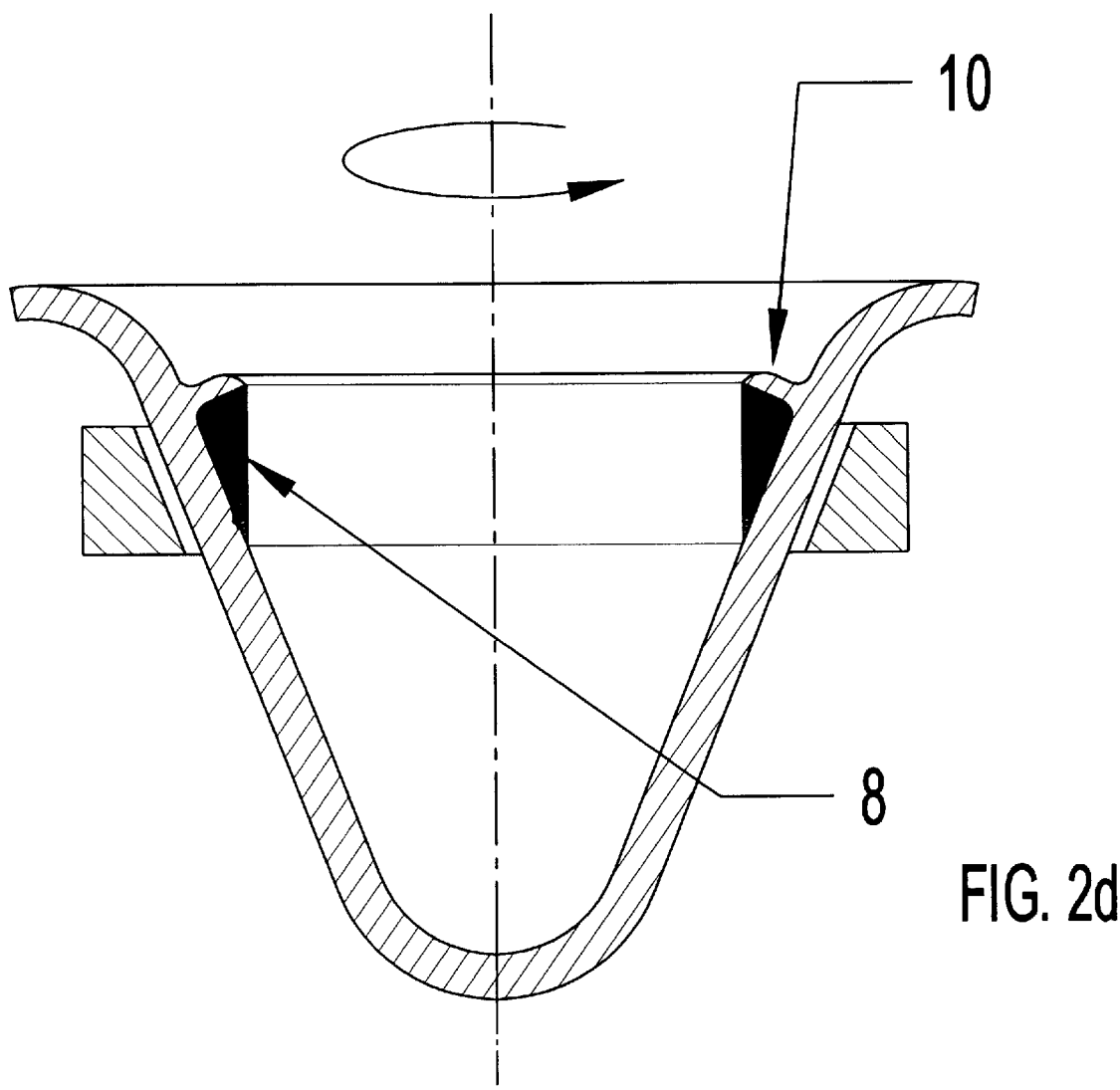
FIG. 2d shows magnetic material being held under a retaining lip by a magnet while the container continues to spin at increased speed with substantially all supernatant expelled in accordance with an embodiment of the present invention.

FIG. 2d illustrates the final stages of separation where clump 8 is tightly packed under lip 10 and continuing centrifugal force serves to further extract water from the consolidated mass.

Figure 3:
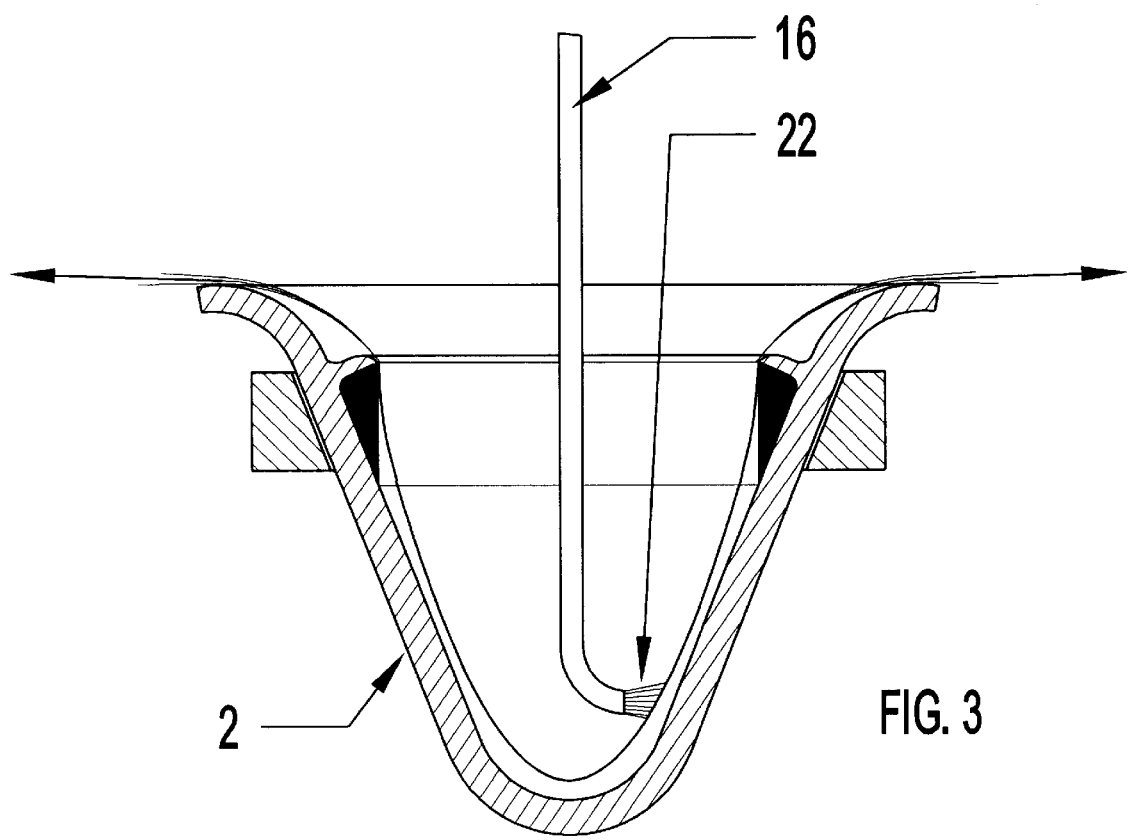
FIG. 3 shows magnetic material being held under a retaining lip by a magnet and a portion of the container being rinsed while continuing to spin at high speed in accordance with an embodiment of the present invention.

FIG. 3 illustrates the final stages of the extraction wash process where dispensing probe 16 enters container 2 and slowly dispenses rinse solution 22 into the container while container continues to rotate at moderate speed. It can be appreciated by those familiar with centrifugal separation that maintenance of centrifugal and magnetic force on the clump while directing a stream into the container will not dislodge magnetic material or break up the clump so long as magnetic and centrifugal forces exceed hydrodynamic loads imposed by stream 22. Concurrent dispensing of stream 22 and application of centrifugal and magnetic force provides the means to rinse away nearly all traces of unbound material during a single wash cycle.

Figure 4:
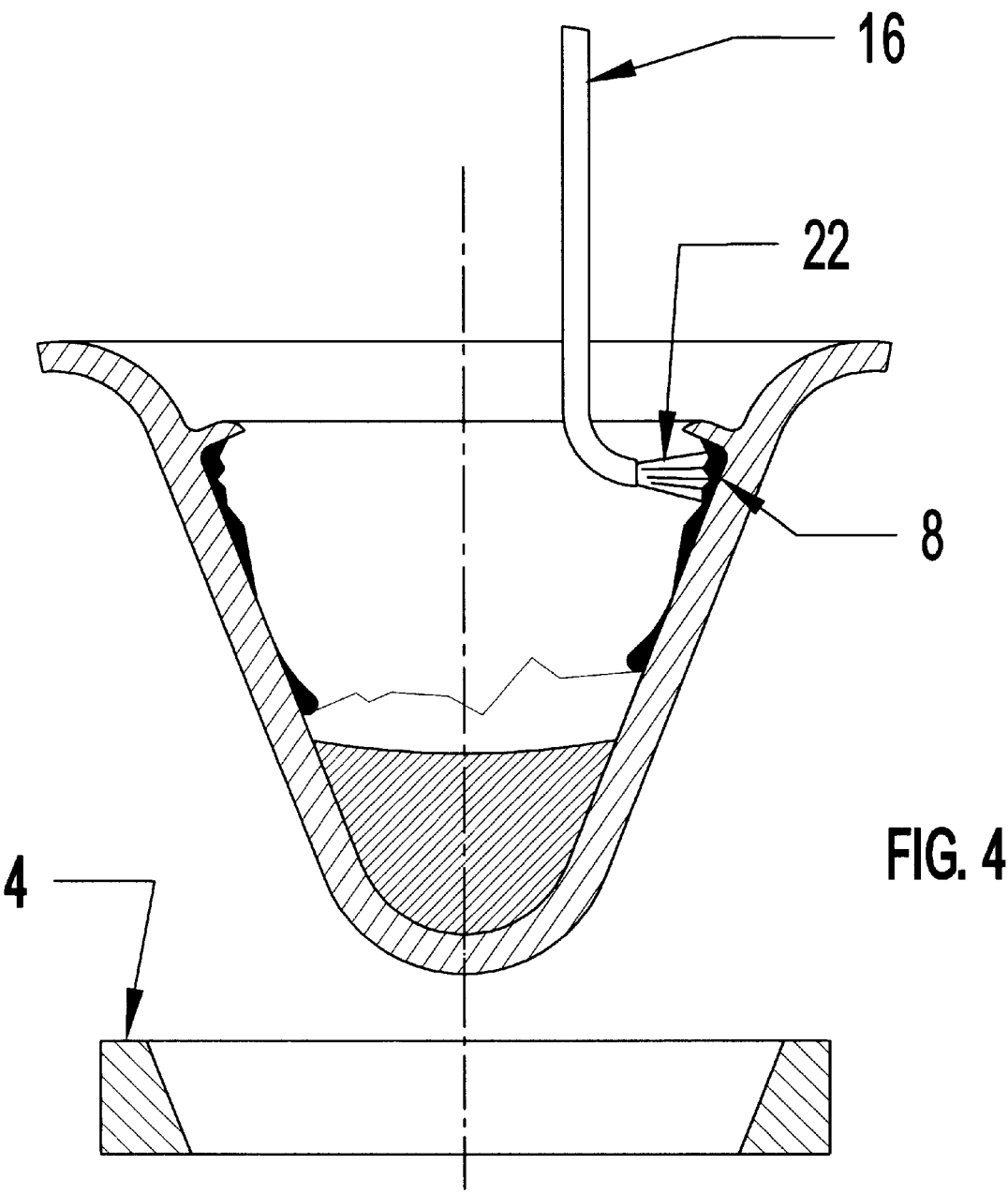
FIG. 4 shows a portion of the container being rinsed while spinning a slow speed such that the magnetic material is dislodged with a magnet removed from influence over the magnetic material in accordance with an embodiment of the present invention.

FIG. 4 illustrates the final re-suspension phase of a wash cycle. Magnet 4 is removed from influence over clump 8. Probe 16 is moved to a position to direct stream 22 directly against clump 8. Cup rotational velocity slows and stream velocity 22 increases until hydrodynamic forces exceed centrifugal and cohesion forces within the clump, whereupon, the clump begins to break up and return to solution. Liquid addition continues until a desired aliquot is achieved to satisfy the next phase of the assay or sufficient liquid is present to assure complete re-suspension. Container 2 may be rotated in a back and forth pattern or similarly agitated to achieve and preserve full suspension of particles.

The cycle may be repeated on the same sample to further reduce the levels of unbound, unwanted material and thereby increase the purity of material captured by the magnetic particles.

The bond between the analyte of interest and magnetic particles may broken or de-coupled by heat, surfactant or other means common in the art, once the desired purity of assay is achieved. Re-application of magnetic force serves to separate and pull unbound particles out of solution leaving a purified sample of material extracted by means of the above described wash process. Highly purified material is thus available within the cup as supernatant for further assay.

While there have been described what are believed to be the preferred embodiments of the invention, those skilled in the art will recognize that other and further modifications may be made thereto without departing from the invention and it is intended to claim all such changes and modifications as fully within the scope of the invention.

I claim:

1. A method for separating a component of interest from a sample, said method comprising:

providing a container;

said container having a longitudinal axis, an interior volume, and a physical feature for trapping and retaining at least a portion of a particulate material disposed within said interior volume of said container when said container is rotated about said longitudinal axis of said container;

disposing, within said interior volume of said container, both of said sample and a multiplicity of magnetic particles, said magnetic particles being coated with a reaction component that binds with said component of interest;

mixing said sample with said multiplicity of coated magnetic particles to thereby produce a mixture of said magnetic particles and a supernatent liquid; and thereafter, separating said magnetic particles from said supernatent liquid by:

centrifuging said mixture of magnetic particles and supernatent liquid within said container by rotating said container about said longitudinal axis such that at least a portion of said supernatent liquid is expelled from said container while at least a portion of said multiplicity of magnetic particles are trapped and retained within said interior volume of said container by said physical feature; and applying a magnetic field to said container such that magnetic lines of force penetrate said container and pass through said mixture of said magnetic particles and said supernatent liquid during at least a portion of said centrifuging of said mixture of magnetic particles and supernatent liquid within said container.

2. The method of claim 1, further comprising the steps of:

rotating said container about said longitudinal axis at low speeds while directing a rinse liquid at magnetic particles previously held in place by said magnetic lines of force, thereby loosening and re-suspending said bound particles into said rinse liquid; and substantially ceasing rotation of said container about said longitudinal axis.

3. The method of claim 2, wherein said magnetic lines of force penetrate said container at varying positions along said longitudinal axis of said container.

4. The method of claim 2, wherein said steps of:

centrifuging said mixture of magnetic particles and supernatent liquid within said container by rotating said container about said longitudinal axis; and applying a magnetic field to said container;

are independently controlled to suit at least one hydrodynamic characteristic of said sample.

5. The method of claim 2, wherein said steps of:

centrifuging said mixture of magnetic particles and supernatent liquid within said container by rotating said container about said longitudinal axis; and applying a magnetic field to said container;

are modulated in relative unison to suit at least one hydrodynamic characteristic of said sample.

6. The method of claim 2, wherein said container is a generally circular container.

7. The method of claim 2, wherein said sample is a biological sample.

8. The method of claim 1, wherein said magnetic lines of force penetrate said container at varying positions along said longitudinal axis said container.

9. The method of claim 1, wherein said steps of:

centrifuging said mixture of magnetic particles and supernatent liquid within said container by rotating said container about said longitudinal axis; and applying a magnetic field to said container;

are independently controlled to suit at least one hydrodynamic characteristic of said sample.

10. The method of claim 1, wherein said steps of:

centrifuging said mixture of magnetic particles and supernatent liquid within said container by rotating said container about said longitudinal axis; and applying a magnetic field to said container;

are modulated in relative unison to suit at least one hydrodynamic characteristic of said sample.

11. The method of claim 1, wherein said container is a generally circular container.

12. The method of claim 1, wherein said sample is a biological sample.

13. The method of claim 1, wherein:

said container includes a peripheral wall substantially encircling said interior volume of said container; and said physical feature for trapping and retaining at least a portion of a particulate material disposed within said interior volume of said container comprises a lip portion extending radially inward toward said longitudinal axis of said container from said peripheral wall of said container.

14. The method of claim 13, wherein:

said container has a bottom base portion and a top rim portion; and said peripheral wall of said container slopes substantially radially outward from said bottom base portion to said top rim portion.

15. The method of claim 1, wherein said sample and said multiplicity of magnetic particles are mixed within said interior volume of said container.

\* \* \* \* \*